US009649195B2

(12) United States Patent
Bechtold et al.

(10) Patent No.: US 9,649,195 B2
(45) Date of Patent: May 16, 2017

(54) FEMORAL IMPLANT FOR PRESERVING CRUCIATE LIGAMENTS (75) Inventors: Kevin Bechtold, Miami, FL (US); Ali Zafar Abbasi, Davie, FL (US); Amit Mistry, Plantation, FL (US); Mark Ellsworth Nadzadi, Memphis, TN (US); Jason Karl Otto, Plantation, FL (US)

(73) Assignee: Mako Surgical Corp., Fort Lauderdale, FL (US)

( * ) Notice: Subject to any disclaimer, the term of this patent is extended or adjusted under 35 U.S.C. 154(b) by 0 days.

(21) Appl. No.: 13/340,636

(22) Filed: Dec. 29, 2011

(65) Prior Publication Data
US 2013/0173008 A1    Jul. 4, 2013

(51) Int. Cl.
*A61F 2/38*    (2006.01)
*A61F 2/30*    (2006.01)

(52) U.S. Cl.
CPC ........ *A61F 2/3859* (2013.01); *A61F 2/30771* (2013.01); *A61F 2002/3863* (2013.01)

(58) Field of Classification Search
CPC .......... A61F 2/38; A61F 2/461; A61F 2/3859; A61F 2002/3863; A61F 2/3662; A61B 17/1764
USPC ........................................... 623/20.35–20.36
See application file for complete search history.

(56) References Cited

U.S. PATENT DOCUMENTS

| | | | |
|---|---|---|---|
| 4,586,933 A | 5/1986 | Shoji et al. | |
| 5,137,536 A | 8/1992 | Koshino | |
| 5,681,354 A * | 10/1997 | Eckhoff | 623/20.35 |
| 5,728,162 A | 3/1998 | Eckhoff | |
| 7,918,893 B2 * | 4/2011 | Romeis et al. | 623/20.24 |
| 7,998,203 B2 * | 8/2011 | Blum | 623/13.12 |
| 8,066,776 B2 | 11/2011 | O'Connor et al. | |
| 8,163,028 B2 * | 4/2012 | Metzger et al. | 623/20.36 |
| 2004/0204760 A1 * | 10/2004 | Fitz et al. | 623/14.12 |
| 2008/0140212 A1 | 6/2008 | Metzger et al. | |
| 2009/0062925 A1 * | 3/2009 | Samuelson | 623/23.12 |
| 2009/0076604 A1 | 3/2009 | Linares | |
| 2009/0132055 A1 * | 5/2009 | Ferro | 623/20.21 |
| 2009/0306783 A1 | 12/2009 | Blum | |
| 2010/0305709 A1 * | 12/2010 | Metzger et al. | 623/20.27 |
| 2010/0305710 A1 | 12/2010 | Metzger et al. | |
| 2011/0264097 A1 | 10/2011 | Hodorek et al. | |

(Continued)

FOREIGN PATENT DOCUMENTS

EP    1 174 099    1/2002
GB    2 464 862    5/2010

OTHER PUBLICATIONS

International Search Report and Written Opinion for International Application No. PCT/US2012/070930, mailed May 27, 2013, 16 pages.

(Continued)

*Primary Examiner* — Ann Schillinger
(74) *Attorney, Agent, or Firm* — Lerner, David, Littenberg, Krumholz & Mentlik, LLP (57) ABSTRACT A femoral prosthetic component comprises a pair of condyles having an intercondylar notch interposed substantially therebetween. Each of the pair of condyles comprises an edge that borders the intercondylar notch. At least one of the pair of condyles comprises a condylar notch disposed within the respective edge of the at least one of the pair of condyles.

6 Claims, 8 Drawing Sheets

(56) References Cited

U.S. PATENT DOCUMENTS

| | | |
|---|---|---|
| 2012/0078262 A1 | 3/2012 | Pinczewski et al. |
| 2012/0179266 A1 | 7/2012 | Collazo |
| 2012/0185055 A1 | 7/2012 | Maloney et al. |
| 2012/0209394 A1 | 8/2012 | Bojarski et al. |
| 2012/0323335 A1 | 12/2012 | Parisi et al. |
| 2013/0173008 A1 | 7/2013 | Bechtold et al. |

OTHER PUBLICATIONS

Invitation to Pay Additional Fees and Partial International Search for International Application No. PCT/US2012/070930, mailed Mar. 22, 2013, 6 pages.

Seedhom et al. (Dimensions of the knee.: Ann. rheum. Dis. (1972), 31, 54).

Wada et al. ("Femoral intercondylar notch measurements in osteoarthritic knees." Rheumatology 1999; 38:554-558).

European Search Report for Application No. EP 15174904.1 dated Oct. 8, 2015.

* cited by examiner

FEMORAL IMPLANT FOR PRESERVING CRUCIATE LIGAMENTS

TECHNICAL FIELD

The present disclosure relates generally to orthopedic prosthesis systems used in knee joint replacement surgeries and, more particularly, to a femoral implant for use in knee arthroplasty procedures and associated methods for designing the same.

BACKGROUND

The knee joint comprises the interface between the distal end of the femur and the proximal end of the tibia. In a properly-functioning knee joint, medial and lateral condyles of the femur pivot smoothly along menisci attached to respective medial and lateral condyles of the tibia. When the knee joint is damaged, the natural bones and cartilage that form the joint may be unable to properly articulate, which can lead to joint pain and, in some cases, interfere with normal use of the joint.

In some situations, surgery is required to restore normal use of the joint and reduce pain. Depending upon the severity of the damage, the surgery may involve partially or completely replacing the joint with prosthetic components. During such knee replacement procedures, a surgeon resects damaged portions of the bone and cartilage, while attempting to leave healthy tissue intact. The surgeon then fits the healthy tissue with artificial prosthetic components designed to replicate the resected tissue and restore proper knee joint operation.

One knee replacement procedure—total knee arthroplasty ("TKA")—involves the resection of some or all of each of the medial and lateral condyles of both the femur and tibia and the removal of the fibro-cartilage menisci located at the femorotibial interface. A prosthetic femoral component, typically made of titanium or other strong, surgical-grade metal, is fitted and secured to the distal end of the femur to replace the resected portion of the femur. Similarly, a prosthetic tibial component, the base of which is also typically made of titanium or other suitable metal, is fitted and secured to the proximal end of the tibia to replace the resected portion of the tibia.

In some situations, the patient's bone at the knee joint may have deteriorated to a point which requires TKA surgery, but one or more of the patient's cruciate ligaments (e.g., the anterior cruciate ligament (ACL) and/or posterior cruciate ligament (PCL)) are in sufficient condition to provide adequate joint stability. Maintaining the native cruciate ligaments is often advantageous, as doing so is generally thought to aid in proprioception (the ability to sense where parts of the body are in relation to each other) and could make activities like climbing stairs feel more stable or natural. Preserving the cruciate ligaments can also promote more normal front to back knee motion, which can enhance the patient's ability to maintain pre-operative range of motion, particularly as it relates to deep flexion.

Each of the native cruciate ligaments connects to one of the femoral condyles and passes within the intercondylar region of the femur to connect the center-top portion of the tibia, called the tibial eminence. As such, preserving the cruciate ligaments requires that both the femoral and tibial implant components be configured to allow the cruciate ligaments to pass through the intercondylar area of the joint so that proper function and movement of the native ligaments is substantially preserved. Accordingly, the femoral implant component for cruciate retaining procedures is typically designed with features that replicate the form and function of the medial and lateral condyles of the femur. The medial and lateral components are separated by a deep intercondylar "notch" that allows for passage of cruciate ligaments through the notch. To ensure that the condyles do not interfere with any portion of a ligament during flexion and extension of the femur, some manufacturers design the implant to provide an intercondylar notch having a substantially symmetric "U"-shape having a width that generally corresponds to the widest dimension of the combination of the cruciate ligaments.

Furthermore, some prosthetic implant manufacturers create symmetrical implant components that can be easily scaled to accommodate patients with different bone sizes. Other manufacturers use designs that attempt to simply the shape of the components using combinations of relatively basic lines and arcs. These designs are aimed at reducing costs that are generally associated with the design and manufacture of more complex, anatomically-accurate implant components. For example, the U-shaped design for the intercondylar notch described above reduces the manufacturing complexity that may be associated with more customized designs that attempt to replicate asymmetrical features of the native intercondylar area.

Although the approach for designing the intercondylar notch described above may ensure that the medial and lateral condyle components do not interfere with the cruciate ligaments, it may have several disadvantages. For example, because the combined width of the medial condyle, lateral condyle, and intercondylar notch is limited, an increase in the width of the intercondylar notch requires a corresponding decrease in the width of the medial and lateral condyles of the implant component. Reducing the width of these components may significantly reduce the strength of the femoral implant component.

Furthermore, although simplifying the design of the implant by using symmetrical components or basic "best fit" shapes may reduce manufacturing costs in some situations, such simplification may also lead to components that do not accurately replicate or fit the native anatomy of the joint. For example, certain features of an improperly-sized femoral implant may be larger than the surrounding bone and may impinge upon the surrounding soft tissue. Such imposition of the surrounding soft tissue by the implant, particularly during movement of the implant during flexion and extension of the joint, can cause significant discomfort and may potentially lead to permanent damage to the surrounding soft tissue.

The presently disclosed femoral implant for cruciate retaining knee arthroplasty procedures and methods for designing the same are directed to overcoming one or more of the problems set forth above and/or other problems in the art.

SUMMARY

In accordance with one aspect, the present disclosure is directed to a femoral prosthetic component comprising a pair of condyles having an intercondylar notch interposed substantially therebetween. Each of the pair of condyles may comprise an edge that borders the intercondylar notch. At least one of the pair of condyles comprises a condylar notch disposed within the respective edge of the at least one of the pair of condyles.

According to another aspect, the present disclosure is directed a femoral prosthetic component comprising a pair of condyles having an intercondylar notch interposed substantially therebetween. A shape of the intercondylar notch is asymmetric about a centerline of the femoral prosthetic component and is offset in a lateral direction by about 3 mm to 6 mm from the centerline.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments that, together with the description, serve to explain the principles and features of the present disclosure.

DETAILED DESCRIPTION

Reference will now be made in detail to exemplary embodiments of the present disclosure, examples of which are illustrated in the accompanying drawings. Wherever possible, the same reference numbers will be used throughout the drawings to refer to the same or similar parts.

A healthy knee joint 100 comprises the interface between the distal end of the femur and the proximal end of the tibia. If the healthy knee joint becomes damaged due, for example, to injury or disease, knee surgery may be required to restore normal structure and function of the joint. If the damage to the knee is severe, total knee arthroplasty ("TKA") may be required. TKA typically involves the removal of the damaged portion of joint and the replacement of the damaged portion of the joint with one or more prosthetic components.

Figure 1:
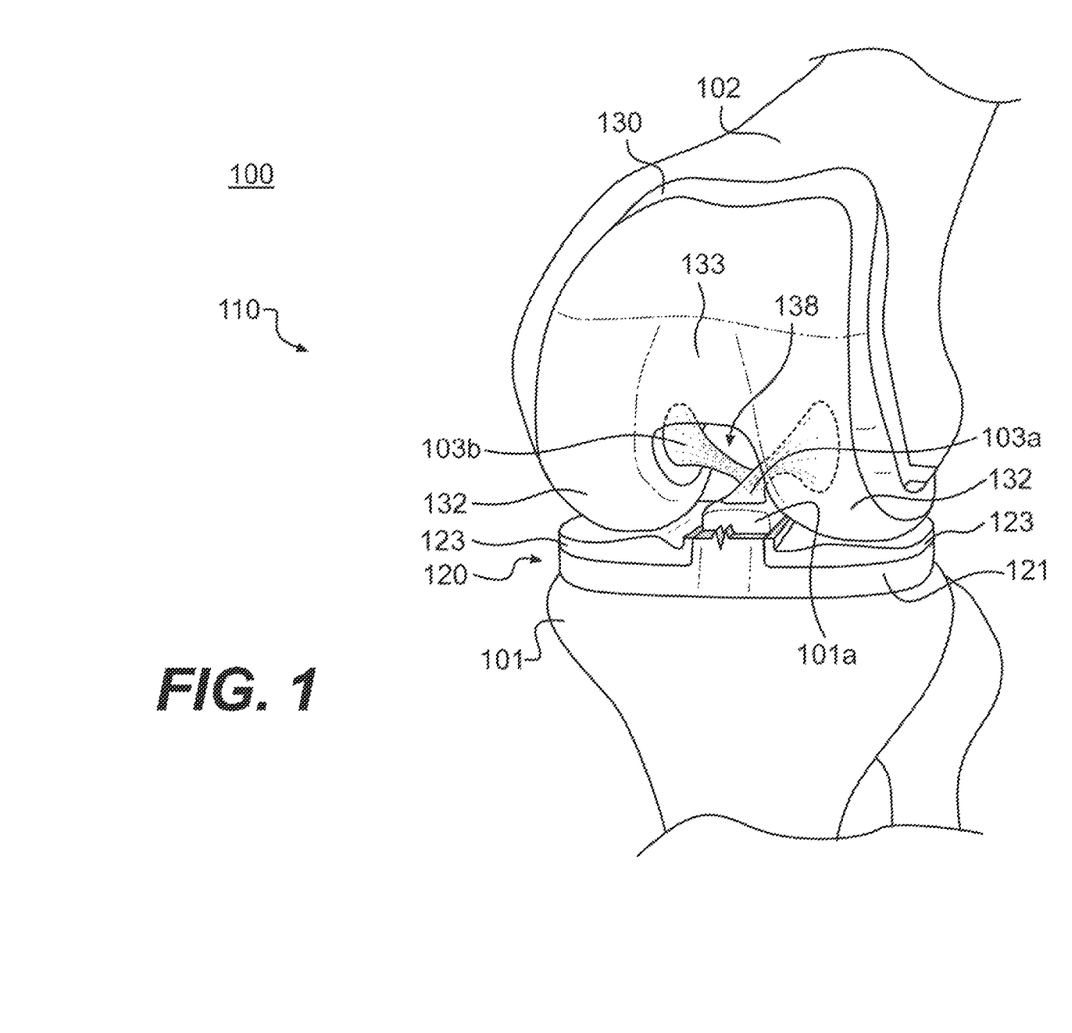
FIG. 1 illustrates a perspective view of post-operative prosthetic knee joint fitted with a cruciate retaining prosthetic system, consistent with certain disclosed embodiments.

To avoid interference with surrounding native tissues, prosthetic components may need to be configured or adapted to closely match the anatomy of the bone to avoid excessive overhang and/or impingement of the implant into the surrounding soft tissues of the joint. For example, in some TKA procedures, one or more of cruciate ligaments 103 (including anterior cruciate ligament 103a and/or posterior cruciate ligament 103b) may be left intact, to be re-used with the prosthetic implants to form the new knee joint. In these "cruciate retaining" applications, the prosthetic implant components may be configured to avoid interference with or impingement on the retained cruciate ligament(s) 103 in the intercondylar area of the knee joint. FIG. 1 illustrates a perspective view of a knee joint 100 fitted with a prosthetic implant system 110, which has been designed using statistical analysis to substantially conform to the anatomy of a population of knee joints.

In the embodiment illustrated in FIG. 1, prosthetic implant system 110 may comprise a plurality of components, each of which is configured to replace a respective resected portion of a native knee joint. According to one embodiment, prosthetic implant system 110 may include a tibial implant system 120 configured to replace a resected portion of a native tibia 101. Prosthetic implant system 110 may also include a femoral component 130 configured to replace a resected portion of a native femur 102. After installation during knee replacement surgery, tibial implant system 120 and femoral component 130 cooperate to replicate the form and function of a native knee joint.

Tibial implant system 120 may include a plurality of components that may be configured to provide a stable surface that articulates with femoral component 130 to restore proper knee joint function. As illustrated in FIG. 1, tibial implant system 120 may include a base portion 121 and one or more insert portions 123. During a knee replacement procedure, base portion 121 may be secured to the proximal end of the tibia 101, which has been surgically prepared by removing damaged bone and tissue and reshaping the healthy bone to receive the base portion 121. Once base portion 121 is secured to tibia 101, the surgeon completes assembly of tibial implant system 120 by engaging and securing insert portions 123 within base portion 121. Base portion 121 of tibial prosthetic system may be configured with a passage through the center to allow for connection between the retained cruciate ligaments 103 and tibial eminence 101a located at the top-center portion of tibia 101.

Femoral component 130 may be secured to the distal end of femur 102 and configured to replace the structure and function of the native femoral portion of knee joint 100. As such, femoral component 130 may be manufactured from surgical-grade metal or metal alloy material (such as surgical-grade steel, titanium, etc.) that is substantially rigid for providing sufficient strength to support the forces required of the knee joint. According to one embodiment, femoral component 130 may embody a single component having a plurality of different structural features, each configured to perform a particular function associated with the knee joint. For example, femoral component 130 may comprise a pair of condyles 132, each of which is coupled to a patellar guide portion 133. The pair of condyles 132 may be separated from one another by an intercondylar notch 133, which provides a channel though which one or more cruciate ligaments 103, such as anterior cruciate ligament (ACL) 103a and/or posterior cruciate ligament (PCL) 103b, may pass.

Figure 2A:
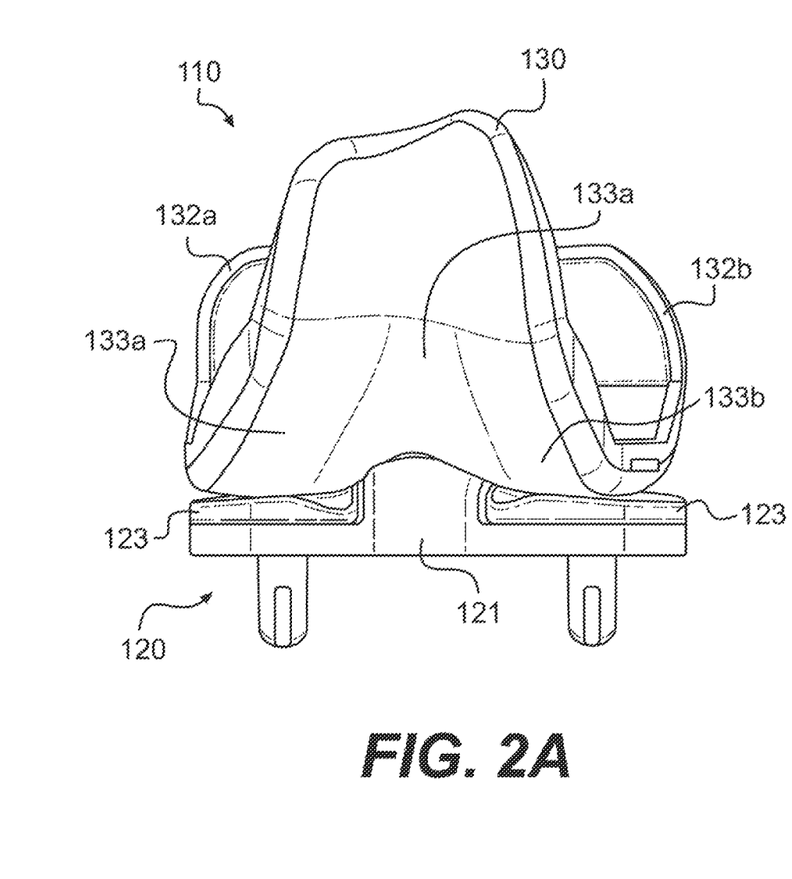
FIG. 2A illustrates a front view of a cruciate retaining prosthetic system, in accordance with an exemplary embodiment.
Figure 2B:
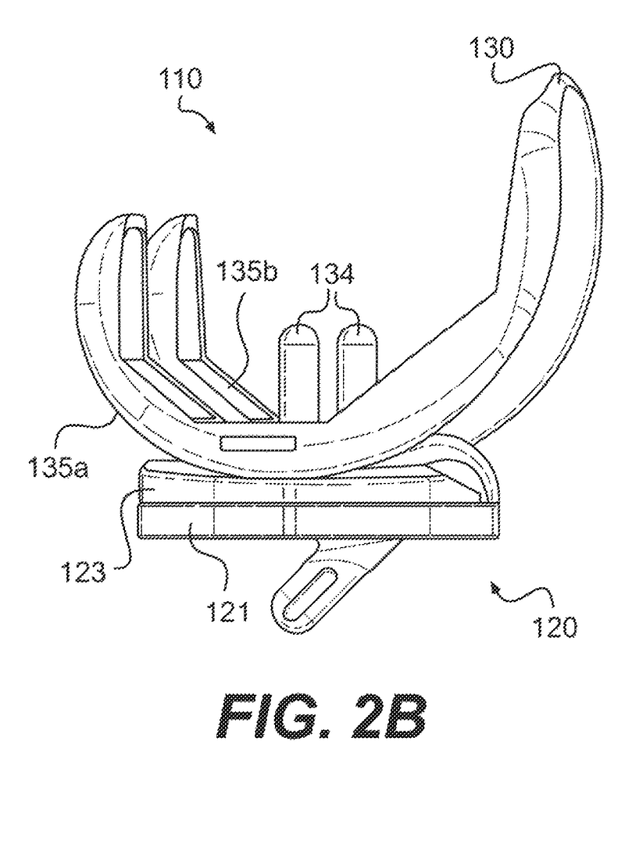
FIG. 2B illustrates a side view of the cruciate retaining prosthetic system shown in FIG. 2A, consistent with certain exemplary disclosed embodiments.

FIGS. 2A and 2B provide respective front and side views of an exemplary prosthetic implant system 110. As noted above, prosthetic implant system 110 includes femoral component 130 that is configured to engage and articulate with insert portions 123 of base portion 121. During use, the femur is rotated relative to the tibia during flexion and extension, causing femoral component 130 to rotate relative to base portion 121 across the top surface of insert portions 123.

As explained above, femoral component 130 comprises a patellar guide portion 133 and a pair of condyles 132, including a medial condyle 132a and a lateral condyle 132b. Patellar guide portion 133 of femoral component 130 may extend from the front of the distal end of the femur and curve downward toward the intercondylar fossa of the femur, which is exposed by intercondylar notch 138. Medial and lateral condyles 132a, 132b project from the bottom of patellar guide portion 133 and extend on either side of intercondylar notch 138 around the underside of the femur and continuing toward the posterior of the femur.

As shown in FIG. 2B, femoral component 130 includes a bearing surface 135a and an interface surface 135b. Bearing surface 135a comprises a curved, outward-facing (inferior) surface formed by patellar guide portion 133 and condyles 132. Accordingly, bearing surface 135a is configured to articulate with one or more features of the knee joint, such as the patella (not shown) and insert portions 123 of tibial implant system 120.

Interface surface 135b comprises the inner (superior) surface of femoral component 130 and is configured to engage with and attach to the resected surface of femur 102. According to one embodiment, interface surface 135b may comprise a plurality of planar surfaces, each of which corresponds to a resected plane of the femur that has been prepared using a planar cutting tool. Although illustrated as having a plurality of planar surfaces, it is contemplated that interface surface 135b may be configured as having any shape suitable for engagement with a resected surface of the femur. Accordingly, in the event that the resected surface of the femur comprises a substantially curved shape, interface surface 135b may be substantially curved to match the resected surface of the femur.

Femoral component 130 may also comprise one or more elongated projections 134 that protrude from internal surface 135b. Elongated projections 134 may be inserted into corresponding holes that have been surgically formed within femur 102 during a TKA procedure. Elongated projections 134 may be secured within the holes and configured to limit movement between femoral component 130 and femur 102.

Patellar guide portion 133 of femoral component 130 may be configured to emulate the structure and function of the native patellar surface, which is located on the front of the distal end of femur 102. For example, patellar guide portion 133 includes a median groove 133a that is located toward the center of patellar guide portion 133. Located on either side of median groove 133a and directly above respective condyles 132a, 132b are a plurality of raised surfaces 133b, 133c. Median groove 133a provides the surface that articulates with the patella (or "kneecap," not shown), while raised surfaces 133b, 133c prevent the patella from sliding outside of median groove 133a.

As explained, condyles 132 may comprise medial condyle 132a and lateral condyle 132b. Condyles 132 are configured to replace the structure and function of the corresponding native condyles of the femur. As such, condyles 132 project from the lower portion of patellar guide portion 133 on the anterior side of femur 102, curve around the underside of femur 102, and extend to the posterior side of femur 102. Condyles 132 are configured to provide the primary structural and articular support for the femoral component of the knee joint.

Figure 3:
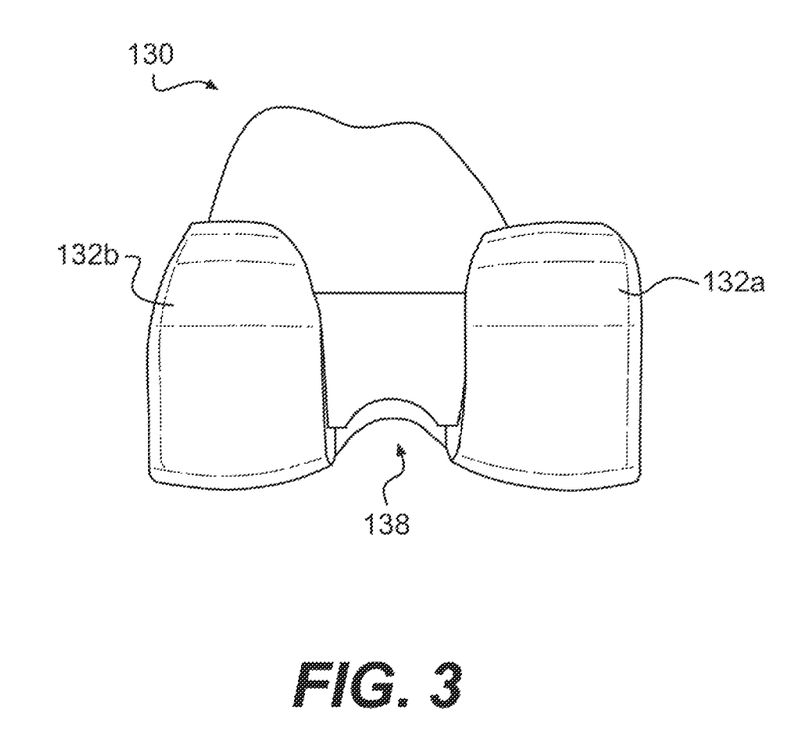
FIG. 3 provides rear view of a femoral prosthetic component of a cruciate retaining prosthetic system, in accordance with certain disclosed embodiments.

As will be explained in greater detail below, femoral component 130 may be semi-customized using statistical analysis to fit a particular population of potential patients. As such, femoral components 130 that are designed consistent with the disclosed embodiments provide a more custom fit than many conventional implants, which are designed to maximize symmetry for ease of manufacture and versatility of use. FIG. 3 illustrates a rear view of a femoral component designed with processes consistent with the disclosed embodiments.

Methods for designing prosthetic implants consistent with the disclosed embodiments may render an implant having asymmetric component features that are customized to fit the anatomy of a specific population of patients within a threshold level of accuracy. For example, as illustrated in FIG. 3, methods consistent with the disclosed embodiment may render medial and lateral condyles 132a, 132b of femoral component 130 that have substantially irregular, asymmetric component features, the shapes of which are statistically fit to the anatomy of a population of patients that have similar bone characteristics. As a result, in contrast with conventional implant systems having standard, symmetrically shaped component features, the presently disclosed femoral components 130 and associated methods provide semi-custom implants that are designed to more precisely emulate the irregularly-shaped anatomy of the end of the femur.

Figure 4:
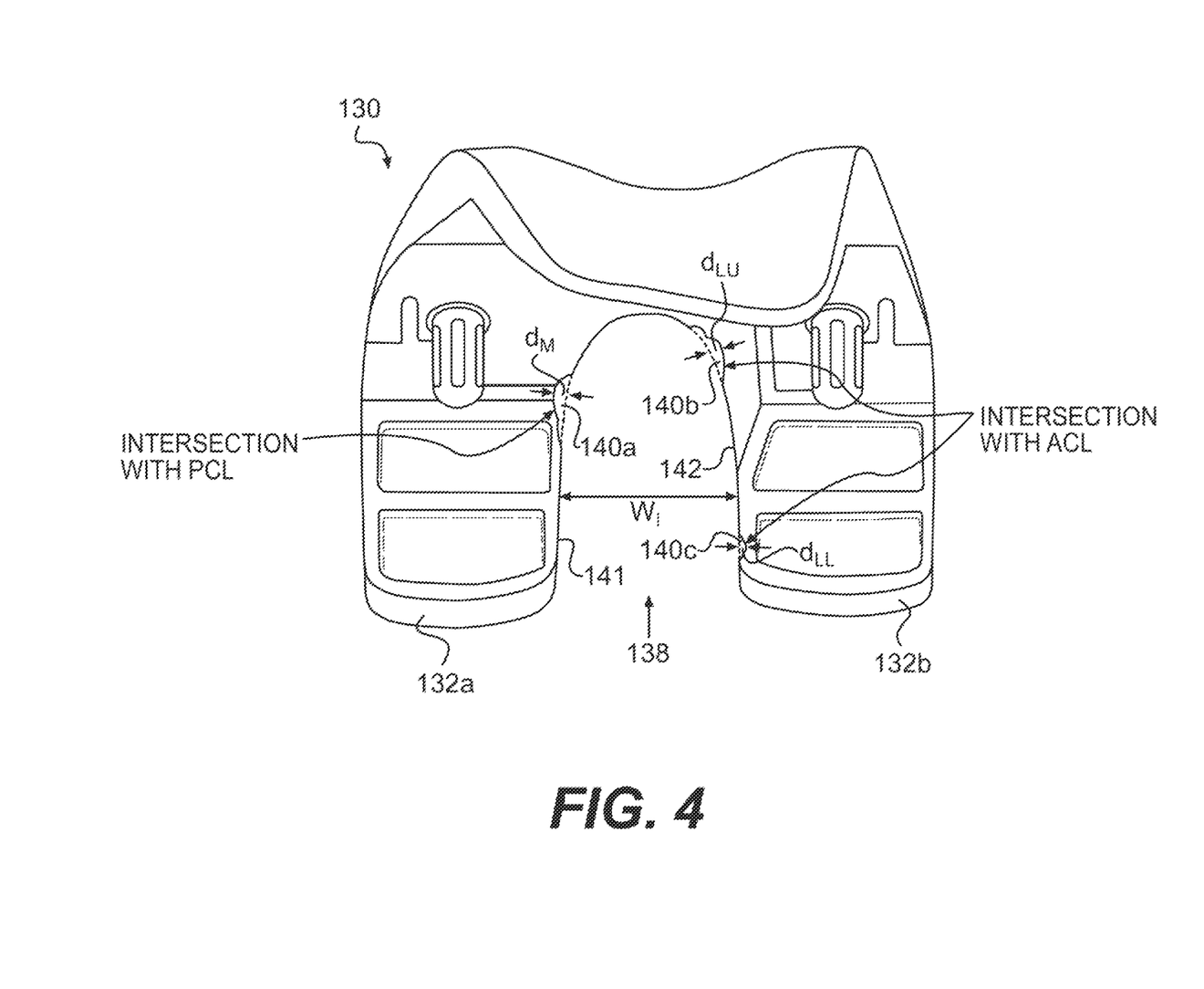
FIG. 4 provides a top view of a femoral prosthetic component of a cruciate retaining prosthetic system, consistent with the disclosed embodiments.

As an alternative or in addition to tailoring the femoral component 130 to match the bone anatomy as shown in FIG. 3, the presently disclosed methods provide a solution for designing femoral component 130 to accommodate the anatomy of certain soft tissues. For example, for implants used in cruciate-retaining procedures, it may be necessary to ensure that portions of femoral component 130 do not inhibit, interfere with, or damage the retained cruciate ligaments. To remedy this, most implant manufacturers simply increase the width of intercondylar notch 138 between condyles 132. This increase typically requires a corresponding decrease in the widths of condyles 132. Decreasing the width of condyles 132 may result in a decrease in the overall strength of the implant, increasing the likelihood of a failure of femoral component 130. FIG. 4 illustrates an exemplary femoral component 130, which has been designed to match the anatomy of both hard tissue (e.g., bone) and certain soft tissues (e.g., cruciate ligaments).

As shown in FIG. 4, femoral component 130 comprises one or more condylar notches 140, including one or more medial condylar notches 140a and/or one or more lateral condylar notches 140b, 140c. The size, shape, and location of condylar notches 140 are configured to prevent the edges of femoral component 130 from contacting or otherwise interfering with the cruciate ligaments. By providing condylar notches 140, methods consistent with the disclosed embodiments are able to provide anatomically matched cruciate retaining implant—one that does not interfere with the retained cruciate ligament, without unduly reducing the strength of condyles 132.

Medial condylar notch 140a may be located at the inner (or mesial) edge 141 of medial condyle 132a, and may be configured to accommodate at least a portion of a posterior cruciate ligament (PCL) without contacting or otherwise interfering with the ligament. In the embodiment illustrated in FIG. 4, the location of medial condylar notch 140a is designed to correspond to the pose of PCL when the knee joint is at or near full extension. As the knee joint is flexed, the anatomy of the knee joint is such that edge of medial condyle 132a and the PCL gradually separate. Accordingly, the medial condylar notch 140a may gradually become less pronounced toward the posterior of the implant.

It should be noted that size, shape, and location of medial condylar notch 140a illustrated in FIG. 4 is exemplary only and not intended to be limiting. Indeed, it is contemplated that the size, shape, and location of medial condylar notch 140a may vary, depending, for example, on one or more dimensions (e.g., width ($W_I$), depth, etc.) of intercondylar notch 138, the size and position of cruciate ligaments associated with the population of MRI data that was used to create femoral component 130, and/or any threshold tolerances that the designer may include to ensure that medial condyle 132a does not interfere with a cruciate ligament. According to one exemplary embodiment, femoral component 130 may be designed so that the depth, $d_M$, of medial condylar notch 140a is between 1.7 mm and 2.5 mm at its deepest point, which corresponds to a width of intercondylar notch, $W_I$, of approximately 22 mm.

One or more lateral condylar notches 140b, 140c may be located at the inner (or mesial) edge 142 of lateral condyle 132b and may be configured to accommodate at least a portion of a anterior cruciate ligament (ACL) without contacting or otherwise interfering with the ligament. In the embodiment illustrated in FIG. 4, the size and location upper lateral condylar notch 140b is designed to correspond to the pose of ACL when the knee joint is at or near full extension. The size and location of lower condylar notch 140c is designed to correspond to the pose of the ACL when the knee joint is at or near full flexion. As with medial condylar notch 140a, the size, shape, and location of lateral condylar notches 140b, 140c may vary, depending, for example, on one or more dimensions (e.g., width ($W_I$), depth, etc.) of intercondylar notch 138, the size and position of cruciate ligaments associated with the population of MRI data that was used to create femoral component 130, and/or any threshold tolerances that the designer may include to ensure that lateral condyle 132b does not interfere with the ligament. According to one exemplary embodiment, femoral component 130 may be designed so that the depth, $d_{LU}$, of an upper lateral condylar notch 140b is between 1.5 mm and 2 mm at its deepest point, and the depth, $d_{LL}$, of a lower lateral condylar notch 140c is between 1 mm and 1.7 mm.

Those skilled in the art will recognize that the number of condylar notches 140 shown in FIG. 4 are exemplary only and not intended to be limiting. Indeed, fewer condylar notches may be required if, for example, the component design for a particular population of patients requires the placement of the mesial edge 142 of lateral condyle 132b at a position that avoids the possibility of contact with the ACL altogether. In this case, femoral component 130 may not require a lateral condylar notch at all, and may only be designed with a single medial condylar notch 140a.

Alternatively, should, for example, the component design for a particular population of patients require the placement of the mesial edge 141 of medial condyle 132a deeper into the intercondylar area 138, the depth, $d_M$, and length of medial condylar notch 140a may be increased to account the possibility of greater interaction between femoral component 130 and the PCL. In this example, one or more additional medial condylar notches may be required along the mesial edge 141 of medial condyle 132a to avoid additional contact with the PCL as the knee joint is rotated from full extension to full flexion.

As an alternative or in addition to providing condylar notches on the medial and/or lateral condyles within intercondylar notch 138 for accommodating the ACL and/or PCL ligaments, intercondylar notch 138 can be positioned and/or shaped in such a way so as to avoid interference with the ACL and PCL, without necessarily requiring condylar notches. Specifically, because intercondylar notch 138 is the region where both the anterior cruciate ligament (ACL) and posterior cruciate ligament (PCL) pass to attach on the tibia, the intercondylar notch perimeter can be designed (e.g., repositioned or shaped) to accommodate these ligaments for a variety of anatomic geometries associated with different patients.

Figures 5A, 5B:
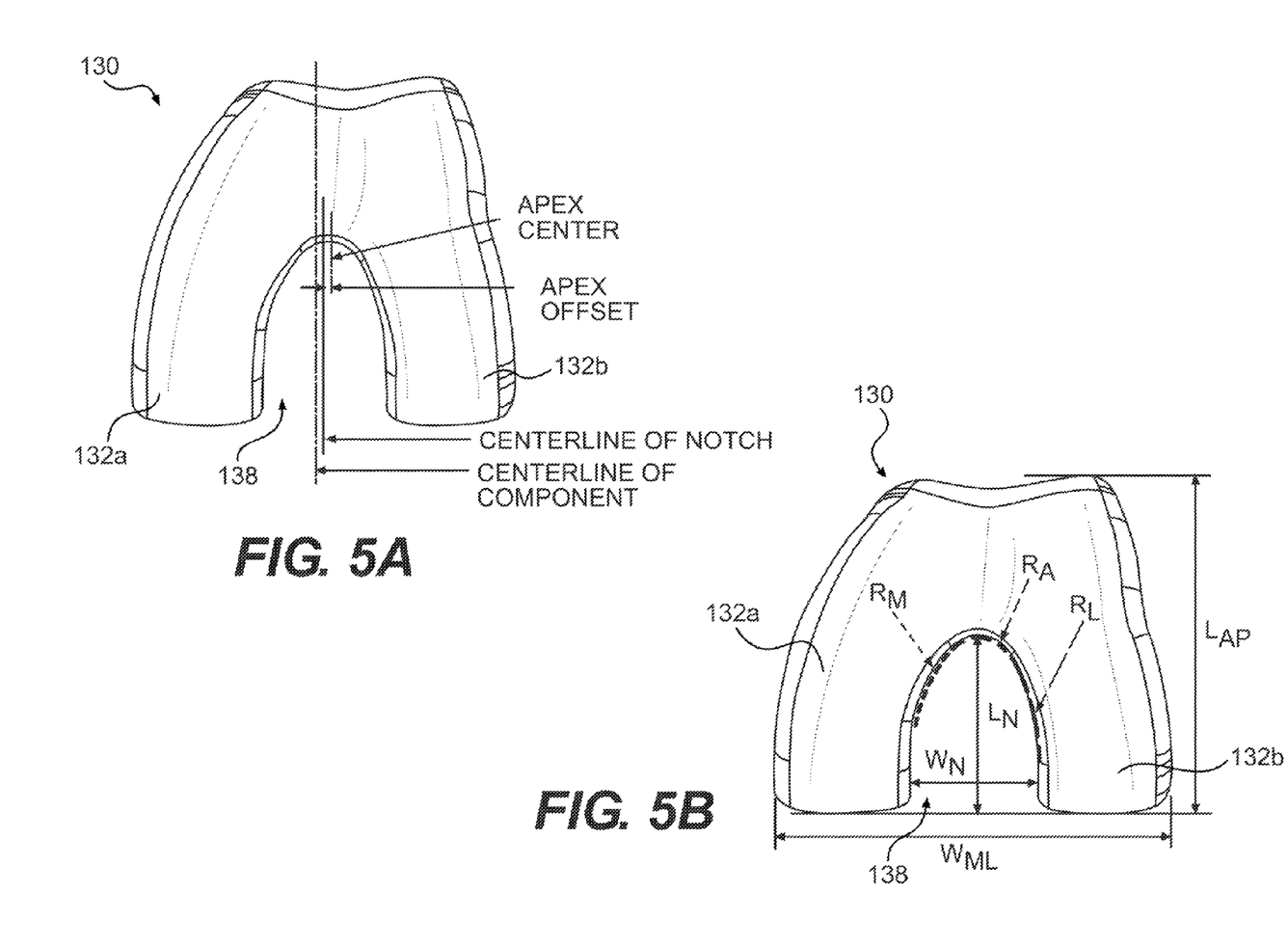
FIGS. 5A-5B provide bottom view of a femoral prosthetic compound of a cruciate retaining prosthetic system displaying certain exemplary features of an intercondylar notch of the prosthetic component, in accordance with certain disclosed embodiments.

As explained, the anterior cruciate ligament typically interacts at the posterior of the lateral condyle of the femur. Consequently, the femoral component intercondylar notch can be laterally shifted to reduce the risk of impingement with the ACL, as shown in FIG. 5A. According to one embodiment, the amount that the notch is laterally shifted from the center of the implant is within the range of 0.5-5 mm, with the ranges in certain exemplary embodiments selected between 0.75-4 mm, with the preferred range between 1 mm and 3 mm.

In addition to the lateral shift in the intercondylar notch, the apex of the femoral component intercondylar notch can also be shifted laterally with respect to the centerline of intercondylar notch 138, as illustrated in FIG. 5A. As with the lateral shift of notch itself, the lateral shift of the apex ranges from about 0.5-5 mm, with certain embodiments ranging from 0.75 mm-4 mm, with the preferred embodiment having a lateral shift between about 1 mm and 3 mm.

According to the embodiment shown in FIG. 5B, the perimeter of intercondylar notch 138 can be generally characterized by three (3) substantially radial arcs, a medial arc ($R_M$), the apex arc ($R_A$), and the lateral arc ($R_L$). The radius of the medial arc ($R_M$) may range from about 15 mm to about 75 mm. According to one embodiment, the radial range may be between 20 mm and 60 mm, with the range of an exemplary embodiment being between 25 mm and 45 mm.

Also as shown in FIG. 5, the radius of the lateral arc ($R_L$) range may be between about 25 mm and 100 mm. According to one exemplary embodiment, the range is between about 30 mm and 80 mm, with the range in a preferred embodiment of between about 35 mm and 60 mm.

According to one embodiment, the apex arc, ($R_A$), may have a radius of between 3 mm and 20 mm, with the preferred range between about 4 mm and 15 mm. According to an exemplary embodiment, the range in radius of the apex arc, ($R_A$), is between about 5 mm and 10 mm.

In order to provide sufficient area for the passage of the ACL and PCL from femur 102 to tibia 101, the width ($W_N$) and length ($L_N$) of intercondylar notch 138 will generally be wider and longer, respectively, than conventional femoral implant components that are not designed to spare the ACL and PCL. According to one embodiment, the width ($W_N$) of intercondylar notch 138 is between about 18 mm and 30 mm, with a preferred range between about 20 mm and 28 mm. In accordance with certain exemplary embodiments, the range in width ($W_N$) is between 22 mm and 26 mm. The length ($L_N$) of intercondylar notch 138 may be between 24 mm and 44 mm, with the preferred range between about 26 mm and 42 mm. In accordance with an exemplary embodiment, length ($L_N$) of intercondylar notch 138 is between about 28 mm and about 40 mm.

In addition to numerical dimensions, the width and the length of intercodylar notch 138 can be expressed in terms of ratios of total medial-lateral component width and total anterior-posterior component length. By expressing the dimensions in terms of ratios rather than numerical dimensions, prosthetic implant 100 may be more easily scaled to accommodate the specific patient needs. According to one embodiment, the width ($W_N$) of intercondylar notch 138 may be about 26-38% of the total width of femoral prosthetic component 130 in a medial/lateral (ML) direction, with a preferred range of between about 28-36% of the total ML width. According to an exemplary embodiment, the width ($W_N$) of intercondylar notch 138 may be about may be about 30-34% of the total ML width. According to one embodiment, the length ($L_N$) of intercondylar notch 138 is about 46-58% of the total length of prosthetic implant 130 in the anterior/posterior (AP) direction, with a preferred range of between about 48-56% of the total AP length. According to an exemplary embodiment, the length ($L_N$) of intercondylar notch 138 is about 50-54% of the total AP length of prosthetic component 130.

Figure 6A:
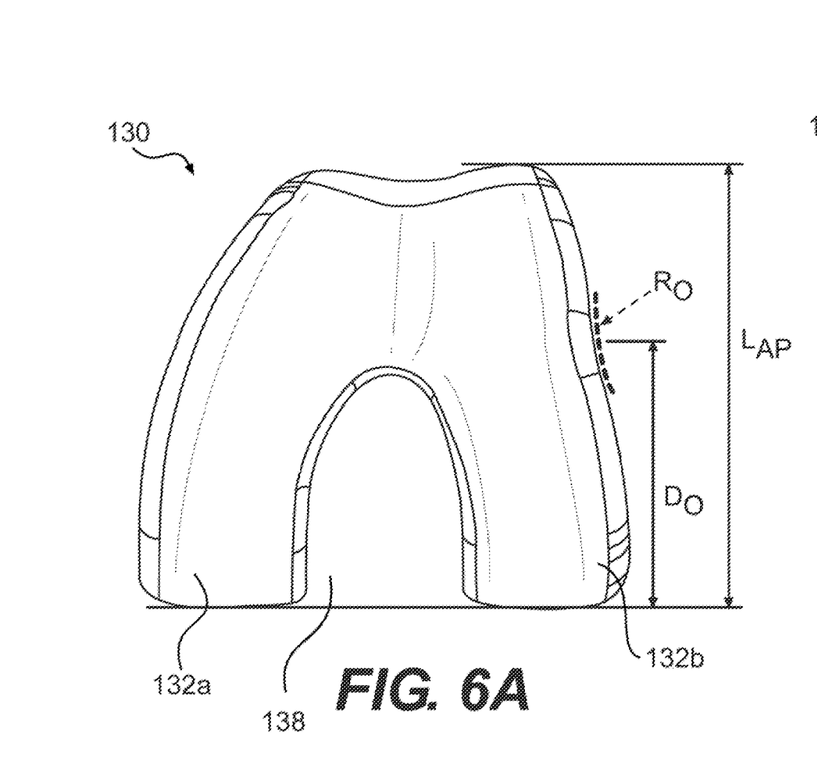
FIGS. 6A-6B provide a bottom view of a femoral prosthetic component of a cruciate retaining prosthetic system displaying certain exemplary features of a meniscal notch of the prosthetic component, consistent with the disclosed embodiments.
Figure 6B:
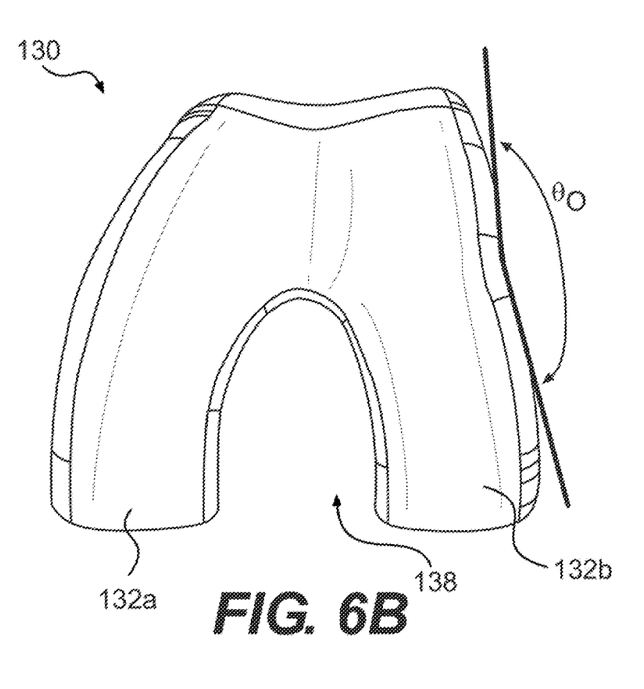

In addition to the ACL and PCL, prosthetic component 130 may be configured to accommodate other soft tissues in and around the knee joint to further avoid impingement of soft tissues. For example, to accommodate for the lateral meniscus when compressed in full extension, prosthetic component 130 may be configured with a meniscal relief notch ($R_O$), as illustrated in FIGS. 6A and 6B. As illustrated in FIGS. 6A and 6B, the femoral component meniscal notch may be characterized by a radial arc that is substantially arcuate in shape. According to one embodiment, the radius that defines the meniscal notch is between about 5 mm and 35 mm, with the preferred range of between about 10 mm and 30 mm. In an exemplary embodiment, the radius range is between about 15 mm and 25 mm.

The location of the center of meniscal notch $R_O$ can be expressed as a distance ($D_O$) from the posterior section of the condyles of the implant. According to one embodiment, the location distance range from the posterior portion of condyles 132a, 132b is between about 26 mm and about 55 mm, with the preferred range of between about 28 mm and 50 mm. According to an exemplary embodiment, the range of length of distance $D_O$ is between about 30 mm and 45 mm, depending upon the size of the patient's anatomy.

The location $D_O$ of the center of meniscal notch $R_O$ can be expressed as a location relative to the total anterior/posterior (AP) length of prosthetic implant 130 measured from the posterior condyles 132a, 132b. According to one embodiment, the location distance $D_O$ of the center of meniscal notch $R_O$ from the posterior condyles is between 51-75% of the AP length of the prosthetic component 130, with a preferred range of between about 53-70% of the AP length of prosthetic component 130. According to an exemplary embodiment, the location distance $D_O$ from the posterior condyles is between about 55-65% of the AP length of the prosthetic component 130.

According to one embodiment, the center of meniscal notch $R_O$ can be characterized by the intersection of substantially straight sections, the intersection of which forms an offset angle $\theta_O$ by which the shape changes to accommodate for the lateral meniscus when compressed in full extension. According to one embodiment the notch radius $R_O$ is selected so as to form an offset angle $\theta_O$ between about 150-179°, with a preferred range between about 155-175°. According to certain exemplary embodiments, the offset angle $\theta_O$ is between about 160-170°.

Figures 7A, 7B, 7C:
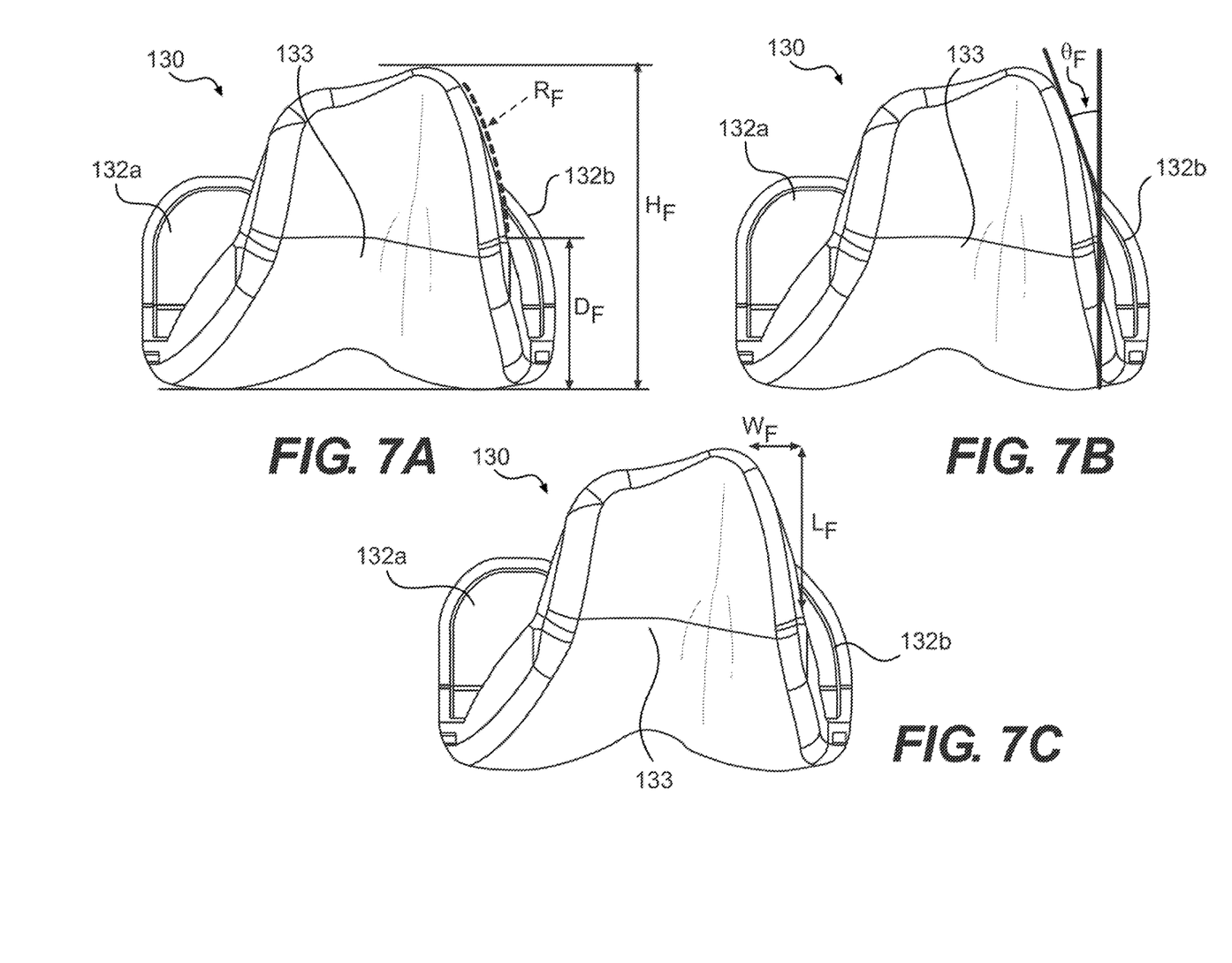
FIGS. 7A-7C provide a front view of a femoral prosthetic component of a cruciate retaining prosthetic system displaying certain exemplary features of an anterior flange of the prosthetic component, in accordance with certain disclosed embodiments.

FIGS. 7A-7C illustrate a front view illustrating an exemplary femoral perimeter shape of an anterior flange, $R_F$, of prosthetic component 130. The shape of the anterior flange $R_F$ is configured to closely match the anatomical profile of resected bone, while avoiding excessive material overhang associated with conventional implants. As illustrated in FIGS. 7A-7C, the anterior flange $R_F$ of femoral component 130 may comprise a substantially arcuate shape defined by a radial arc that starts at a distance $D_F$ above the bottom of prosthetic component 130 and ends at a height $H_F$ located toward the top of prosthetic component 130. According to an exemplary embodiment, the radius of anterior flange ($R_F$) may range from about 15 mm to about 75 mm. According to one embodiment, the radial range may be between 20 mm and 60 mm, with the range of an exemplary embodiment being between 25 mm and 45 mm.

The location $D_F$ of the start point of the radial arc that defines anterior flange ($R_F$) can be expressed as a location relative to the total superior/inferior (S/I) height of prosthetic implant 130. According to one embodiment, the location distance $D_F$ of the is between 45-65% of the SI height of the prosthetic component 130, with a preferred range of between about 48-63% of the SI height of prosthetic component 130. According to an exemplary embodiment, the location distance $D_F$ is between about 50-60% of the SI height of the prosthetic component 130.

According to one embodiment, the anterior flange ($R_F$) can be characterized by the intersection of substantially straight sections, the intersection of which forms an offset angle $\theta_F$ by which the shape changes to accommodate match the anatomical profile of the patient's anatomy. According to one embodiment anterior flange ($R_F$) is established so as to form an offset angle $\theta_F$ between about 0-45°, with a preferred range between about 5-30°. It is contemplated that, in addition to offset angle $\theta_F$, the shape of the anterior flange $R_F$ may also be defined by the length ($L_F$) and width ($W_F$) of the offset created by anterior flange $R_F$.

Figures 8A, 8B, 8C:
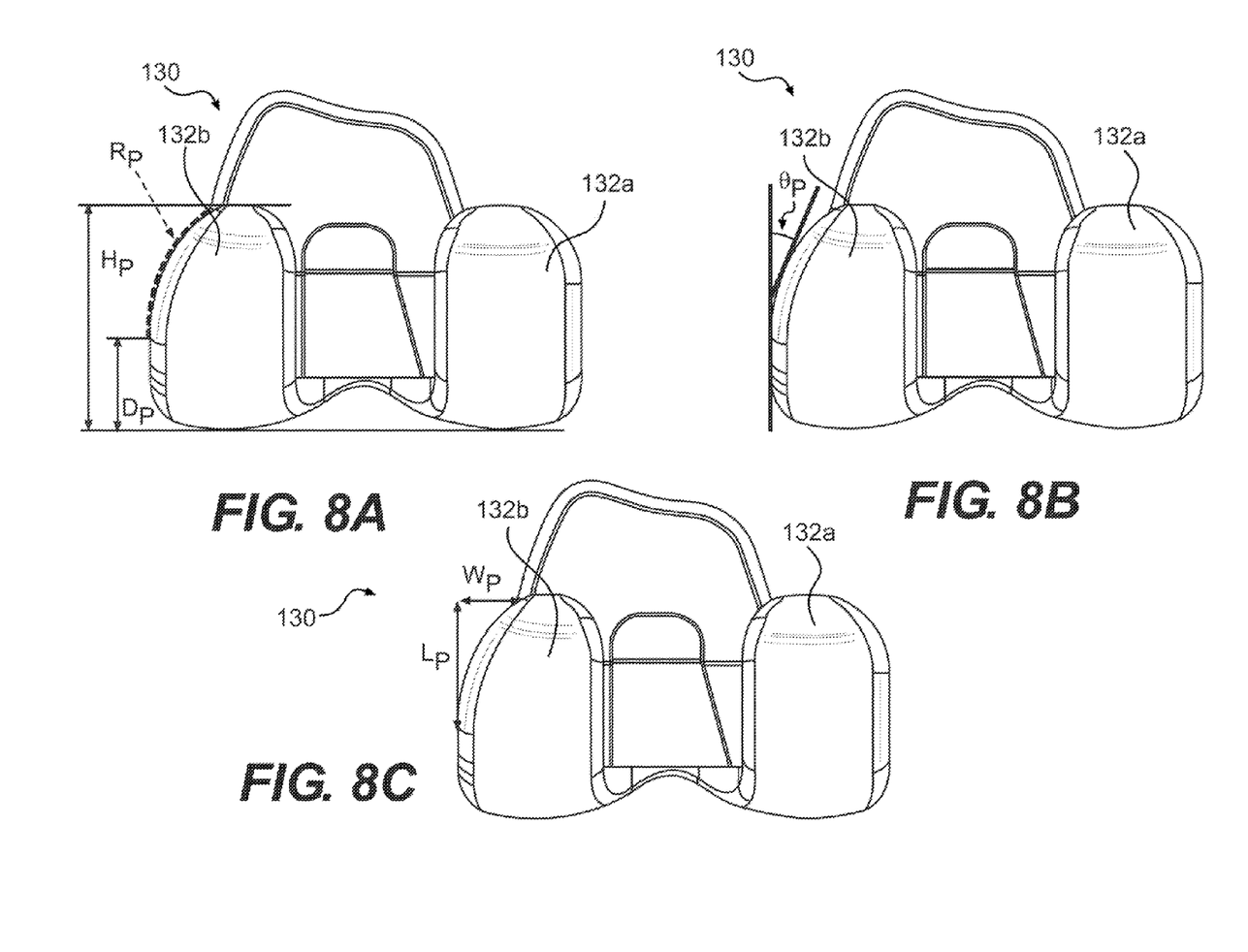
FIGS. 8A-8C provide a rear view of a femoral prosthetic component of a cruciate retaining prosthetic system displaying certain exemplary features of a lateral posterior condyle of the prosthetic component, consistent with the disclosed embodiments.

FIGS. 8A-8C illustrate an exemplary rear view of illustrating an exemplary perimeter shape of a posterior lateral condyle 132b. As illustrated in FIGS. 8A-8C, the posterior of the lateral condyle 132b of femoral component 130 may comprise a substantially arcuate shape defined by a radial arc $R_P$ that starts at a distance $D_P$ above the bottom of prosthetic component 130 and ends at a height $H_P$ located toward the distal end of lateral condyle 132b. According to an exemplary embodiment, the radius of anterior flange ($R_P$) may range from about 15 mm to about 75 mm. According to one embodiment, the radial range may be between 20 mm and 60 mm, with the range of an exemplary embodiment being between 25 mm and 45 mm.

The location $D_F$ of the start point of the radial arc that defines anterior flange ($R_F$) can be expressed as a location relative to the total superior/inferior (S/I) height of lateral condyle 132b. According to one embodiment, the location distance $D_P$ of the is between 20-55% of the SI height of lateral condyle 132b, with a preferred range of between about 25-50% of the SI height of lateral condyle 132b. According to an exemplary embodiment, the location distance $D_P$ is between about 28-45% of the SI height of the prosthetic component 130.

The systems and features described herein provide a solution for designing prosthetic implants that are semi-customized to match the anatomy of a population of patients. The presently disclosed methods and associated femoral implants may have several advantages. For example, implants designed using methodologies consistent with the presently disclosed embodiments are configured to limit interference of the implant with surrounding soft tissues, without unduly compromising material strength. Such embodiments may be particularly advantageous for reducing soft tissue damage and discomfort that is typically associated with conventional implant systems. By reducing soft tissue impingement, the presently disclosed methods may reduce the need for revision surgery, which can significant increase costs and recovery time over the life the implant.

It will be apparent to those skilled in the art that various modifications and variations can be made to the disclosed femoral implants and associated methods for designing the same. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A femoral prosthetic component comprising:
a pair of condyles including a medial condyle and a lateral condyle having an intercondylar notch interposed substantially therebetween, each of the pair of condyles comprising an edge that borders the intercondylar notch wherein the medial condyle includes a medial condylar notch forming a first recess in the edge of the medial condyle that borders the intercondylar notch and the lateral condyle includes a first lateral condylar notch forming a second recess in the edge of the lateral condyle that borders the intercondylar notch,
wherein at least one of the edges of the pair of condyles is characterized by a radial arc and at least one of the first and second recesses interrupts the radial arc in the respective edge of the at least one of the pair of condyles,
wherein the first and second recesses are configured to accommodate a portion of a corresponding cruciate ligament therewithin, without the cruciate ligament contacting the edge of the condyle.

2. The femoral prosthetic component of claim 1, further including a second lateral condylar notch forming a third recess in the edge of the lateral condyle that borders the intercondylar notch.

3. The femoral prosthetic component of claim 1, wherein the femoral prosthetic component further includes a patellar guide component coupled to each of the pair of condyles.

4. The femoral prosthetic component of claim 3, wherein the patellar guide component and each of the pair of condyles comprise a superior surface for engagement with a surface of a femur and an inferior surface for articulation with a bearing surface of a tibial component, and further wherein the medial condylar notch and the first lateral condylar notch each traverses the superior and inferior surfaces of the corresponding condyles.

5. The femoral prosthetic component of claim 1, wherein one of the corresponding cruciate ligaments is an anterior cruciate ligament.

6. The femoral prosthetic component of claim 1, wherein the first and second recesses each define edges that are formed at an angle relative to the respective edge of the corresponding condyles.

* * * * *